United States Patent [19]

Beck et al.

[11] Patent Number: 4,472,975
[45] Date of Patent: Sep. 25, 1984

[54] ULTRASONIC TRANSDUCER COUPLER FOR FLAW DETECTION SYSTEMS

[75] Inventors: Kenneth H. Beck, Newtown, Pa.; Darrell W. Coates, Lawrenceville, N.J.

[73] Assignee: Tac Technical Instrument Corporation, Trenton, N.J.

[21] Appl. No.: 338,750

[22] Filed: Jan. 11, 1982

[51] Int. Cl.³ .............................................. G01N 29/04
[52] U.S. Cl. ..................................... 73/644; 73/642; 73/622
[58] Field of Search .................. 73/644, 624, 622, 642

[56] References Cited

U.S. PATENT DOCUMENTS

| | | | |
|---|---|---|---|
| 2,956,185 | 10/1960 | Von Stocker | 73/644 |
| 3,269,173 | 8/1966 | Ardenne | 73/642 |
| 3,420,097 | 1/1969 | Battermann | 73/644 |
| 3,908,446 | 9/1975 | Mruk | 73/644 |
| 3,938,372 | 2/1976 | Sproule | 73/644 |

FOREIGN PATENT DOCUMENTS 655962 8/1974 U.S.S.R. .
439479 11/1975 U.S.S.R. .

OTHER PUBLICATIONS

KB–Aerotech–Variable Angle Water Column Fixture.
Automation Industries Inc.–Water Coupler & Accessories, 4/69.

*Primary Examiner*—Anthony V. Ciarlante
*Attorney, Agent, or Firm*—Frederick A. Zoda; John J. Kane

[57] ABSTRACT

In the ultrasonic inspection of test pieces, particularly tubular materials, a device for coupling a transducer to the surface of the test material, by a liquid medium, incorporates desirable features of both "contact" and "immersion" transducers. Disclosed is a coupler the housing of which has a cavity having a water supply inlet and an air exhaust vent. Water flow into the cavity if so controlled as to initially purge air from the cavity to fill it with water, after which the water flow is at a carefully controlled rate effective to keep the cavity filled while supplying fresh water only to the extent necessary to make up for water leaking out through a narrow gap defined between the test piece and the face plate of the disclosed coupler. The water within the cavity provides a liquid couplant between the test piece and a transducer carried by a holder mounted in the cavity for precision adjustment. The transducer is in itself adjustable in respect to the holder in each position to which the holder is adjusted. In this way, precision focussing of an ultrasonic beam is attained. Precise control of the incidence and refraction angles of the propagated ultrasonic waves is thereby achieved accompanied by a desirable concentration of the ultrasonic energy in a specific target region of the test piece.

7 Claims, 10 Drawing Figures

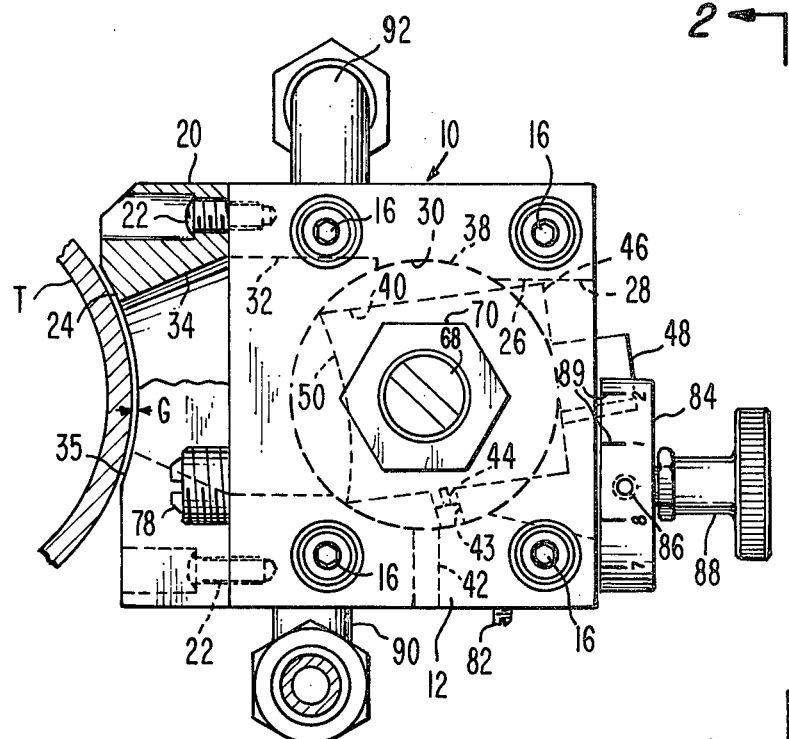
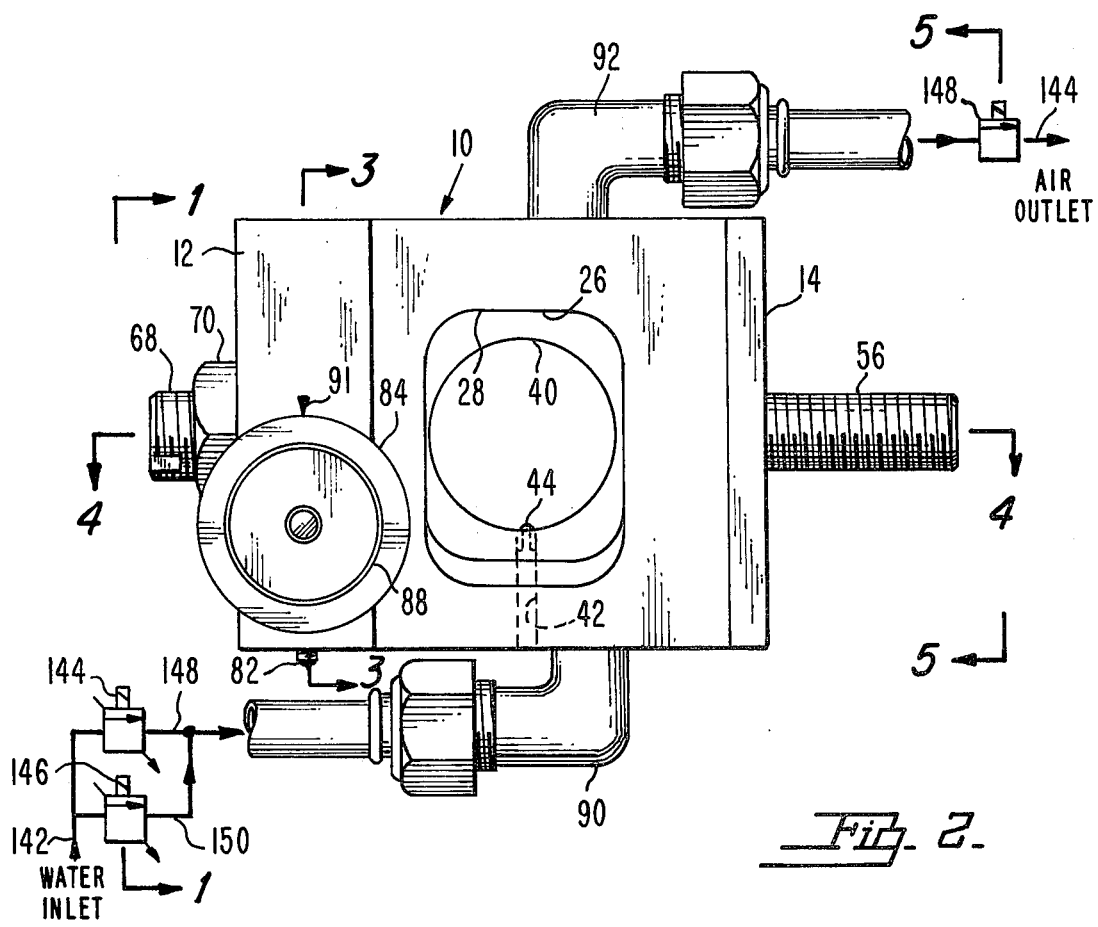

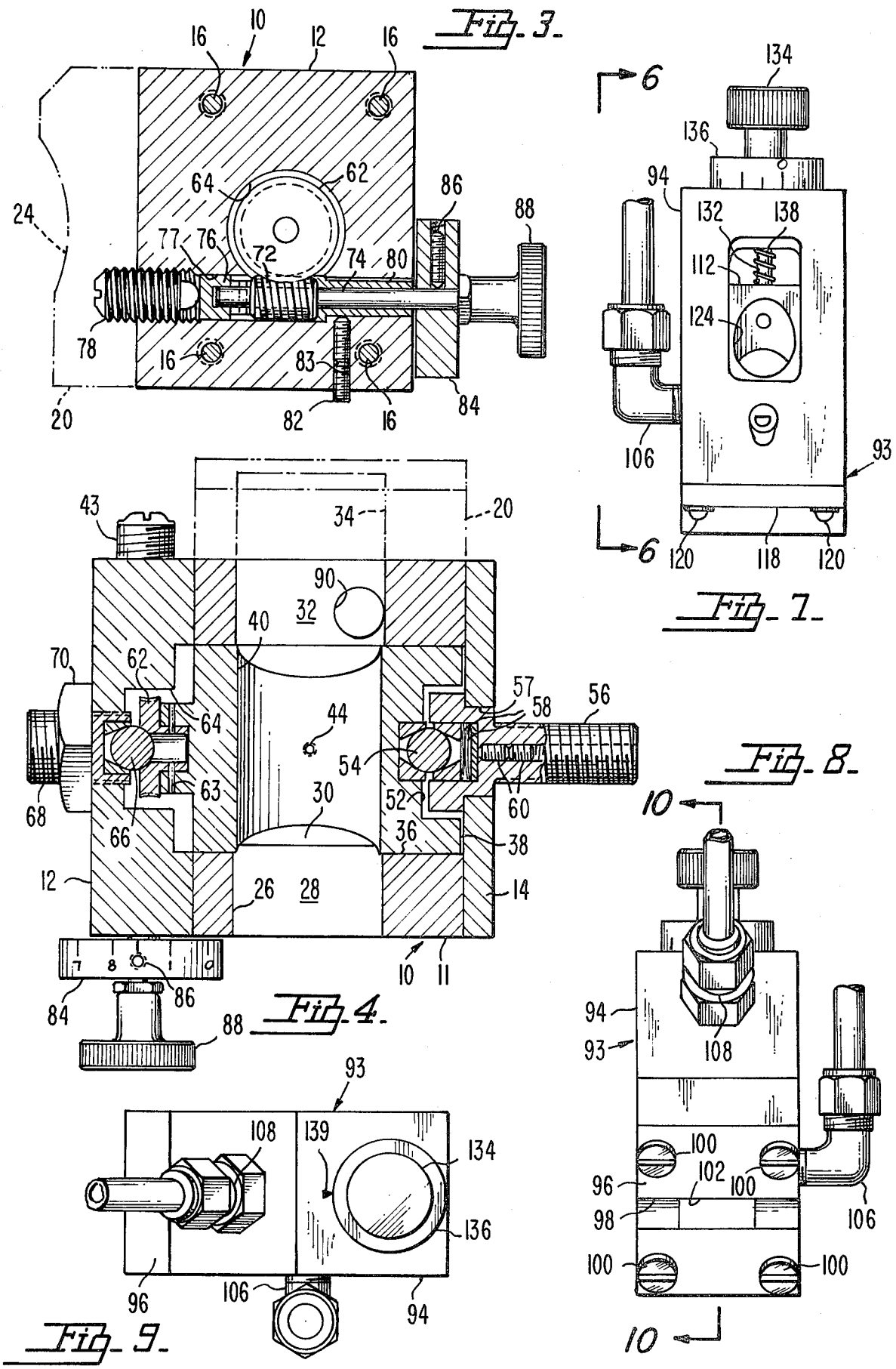

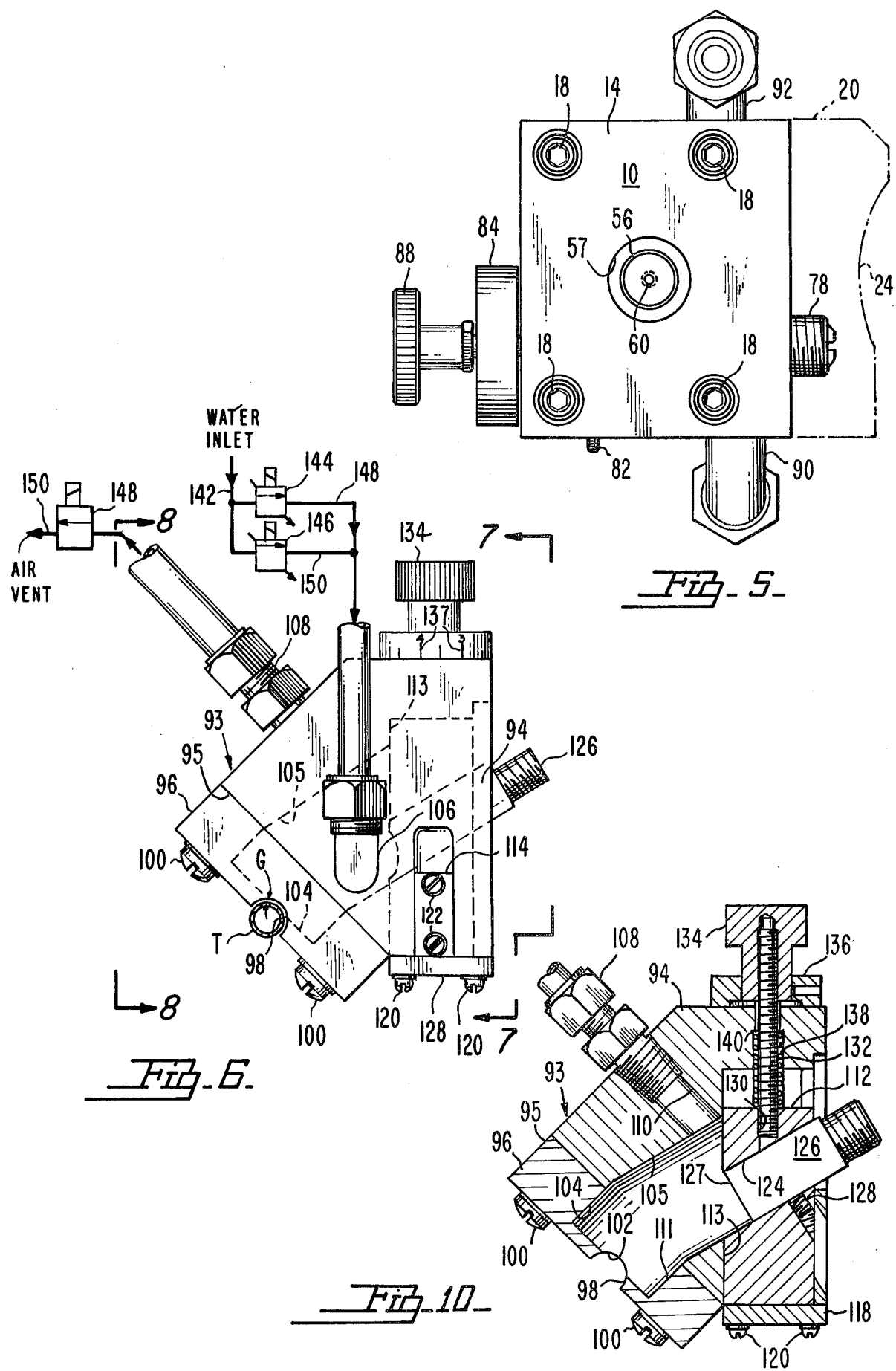

ULTRASONIC TRANSDUCER COUPLER FOR FLAW DETECTION SYSTEMS

BACKGROUND OF THE INVENTION

1. Field of the Invention

The present invention relates generally to measuring and testing systems. In a more particular sense, the invention relates to the art of pipe flaw detection by vibratory means in which ultrasonic waves are beamed against a test piece. Considering the invention with even more particularity, the invention relates to a device of this nature incorporating a transducer scanning means utilizing a liquid (water) couplant.

2. Description of the Prior Art

An ultrasonic inspection transducer is used to transmit high frequency vibrational energy into a piece of test material and to receive signals reflected from the material. In order to do this, the transducer must be "coupled" to the surface of the test material by a medium which will conduct ultrasonic energy efficiently into the material. The coupling medium is generally a liquid so that it can fill and, in effect, "smooth out" microscopic surface irregularities in the transducer face and on the test material surface.

When a transducer is placed directly upon the surface of the material to be tested, a thin film of oil or glycerin is typically used as the couplant. This procedure is called "contact" testing.

Another method of transducer coupling to the test material is called "immersion" testing. In this method, the part to be tested and the transducer are connected by a quantity of water. The water may be either contained in a tank which houses both the transducer and test pieces, or may be in the form of a confined column flowing in such a manner as to continuously connect the surfaces of the transducer and the test material. In the prior art such water column devices have been referred to as "water delay lines", "bubblers", "squirters" or, in the case of very short columns, "gap scanners". (The latter device may perhaps more properly be described as a contact transducer using a water couplant since it does not enable the advantages of true immersion transducers to be realized).

It is often very desirable to utilize focussed ultrasonic beams for inspection. This is especially true when the material is curved or cylindrical in shape, such as tubing and bar stock, but it is also true for certain types of testing of materials with flat surfaces. Both spherically ("point focus") and cylindrically ("line focus") focussed transducers are used. Their proper application results in concentration of the ultrasonic energy in a desired region in the test material, and, often even more importantly, control of the incidence and refraction angles of the ultrasonic wave. This control insures that the ultrasonic wave will propagate in the material in the desired mode (longitudinal, transverse, surface, or "Lamb" waves) and at the desired angle or angles with respect to the material surfaces to provide uniform and sensitive inspection for the types of discontinuities being tested for.

Although not impossible, it is difficult to focus the ultrasonic beam from a contact transducer. This is the case because focussing is usually accomplished by using curved lenses or curved transducer elements and, in general the required radius of curvature for a given desired focal length will not match the surface contour of the part to be inspected.

Focussing of immersion transducers is relatively simple since a lens of the required curvature, often made of plastic, may be cast on to or otherwise attached to the front surface of the transducer. This results in a focussed beam in the coupling water which may then be applied to the part to be tested. Of course, suitable allowance must be made for the relative velocities of propagation of the beam in water and in the test material to determine the focal distance and angle(s) of refraction in the material.

It is broadly known to provide a device for the purposes outlined above, having a self-contained liquid coupling medium. It is also known to provide for angulation of the transducer by mounting it in a spherical member or holder capable of being rotatably adjusted and thereafter locked in a selected position of adjustment. See U.S. Pat. No. 2,956,185.

However, so far as is known the prior art does not contemplate the provision of various features regarded as being of substantial importance. It is important, for example, to provide for a more precise adjustment of the transducer holder in a device of this type than has heretofore been possible. Greater precision in establishing the adjusted position of the transducer holder results in a highly desirable, correspondingly precise angulation of the focussed beam propagated by the transducer.

It is desirable, also, to provide for adjustment of the focal distance through the couplant as measured from the beam propagating surface of the transducer and the target area of the test material, in all positions to which the transducer has been precisely angulated in respect to the test piece surface.

It is a further desirable object to control precisely leakage of the liquid couplant through a gap that necessarily exists between the surfaces of the disclosed device and the test piece.

The prior art, further, is believed to have fallen short of suggesting a device that will permit the ready interchange of face plates to accommodate the device to test pieces of different sizes and contours, while at all times maintaining a precisely established gap in which the above mentioned controlled leakage factor is present.

Finally, the prior art, though broadly suggesting the provision of a confined column of water as a couplant, has been deficient in that maximum efficiency in respect to purging of air has not been achieved.

SUMMARY OF THE INVENTION

The present invention, summarized briefly, in both disclosed examples comprises a housing having a cavity for a water couplant. A water inlet and an air outlet are in communication with the cavity, and these are so positioned relative to the shape and location of the cavity and to each other as to efficiently and swiftly purge air from the cavity during an initial filling of the cavity by water introduced thereto through the inlet.

A face plate is removably secured to the housing, and has a hollow back portion communicating with the cavity to provide, in effect, an extension of the cavity. The face plate is readily removable, to permit free interchange of face plates according to the particular size and contour of the test pieces. The face plate has an opening communicating with the cavity, and it is through this opening that the beams propagated by an ultrasonic transducer are directed against the surface of the test piece.

A transducer holder is mounted within the cavity of the housing for precision adjustment, so as to correspondingly precisely angulate a transducer in respect to the face plate opening and, consequently, the target surface of the test piece exposed through the opening.

A transducer is mounted in the holder for linear adjustment toward and away from the face plate opening, to select the optimum focal distance for the beams propagated thereby, in each and every position to which the transducer may be angularly adjusted responsive to selection of precise, adjusted settings for the transducer holder.

In use, the device is operable through what may be appropriately termed a fill-purge-flow-shutoff cycle in which the cavity is first filled with liquid with a corresponding purging of air, after which an air line through which the air escapes during the filling phase is closed off to aid in maintaining water within the cavity. Thereafter, flow is reduced to no more than that required to make up for leakage of the liquid couplant through the face opening and a narrow gap maintained between the face plate and the test piece surface. Upon removal of the coupler from the test material, all flow of water is switched off to prevent unnecessary water loss.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a side elevational view of one form of a coupler constructed according to the present invention, a work piece being shown fragmentarily and in cross section, and the face plate of the device being partly sectioned away, the device being illustrated as seen from line 1—1 of FIG. 2;

FIG. 2 is a rear elevational view of the device as seen from line 2—2 of FIG. 1, the transducer being omitted, in which control valves for water and air, and their associated piping, are illustrated schematically;

FIG. 3 is a sectional view through the device substantially on line 3—3 of FIG. 2, illustrating the precision adjustment means for the transducer holder, the face plate being illustrated in dotted outline;

FIG. 4 is a sectional view substantially on line 4—4 of FIG. 2, in which the face plate is again shown in dotted outline, the transducer being omitted;

FIG. 5 is a side elevational view as seen from line 5—5 of FIG. 2, showing the side of the device opposite from that seen in FIG. 1, a face plate being shown in dotted outline;

FIG. 6 is a side elevational view of a modified form of the invention, a test piece being illustrated in transverse section, the device being viewed as seen from line 6—6 of FIG. 7, the control valves and their associated piping being illustrated schematically;

FIG. 7 is a rear elevational view of the modification shown in FIG. 6, as seen from line 7—7 of FIG. 6;

FIG. 8 is a front elevational view of the modified device shown in FIG. 6, as seen from line 8—8 of FIG. 6, the work piece being omitted;

FIG. 9 is a top plan view of the modified form of the invention shown in FIG. 6; and FIG. 10 is a sectional view of the modified form of the invention, taken substantially on line 10—10 of FIG. 8.

DETAILED DESCRIPTION OF THE PREFERRED EMBODIMENTS

In the form of the invention shown in FIGS. 1-5 a rectangular housing 10 includes a machined metal block comprising a body portion 11 to opposite sides of which a gear box 12 and stud plate 14 are fixedly secured by screws 16, 18 respectively.

A face plate 20 is secured to the front surface of body portion 11 by rectangularly spaced screws 22, and has a concavely contoured face 24 shaped complementarily to the convex surface of a test piece T which in the present instance would be a tube, thereby assuring uniformity in a narrow gap G defined (FIG. 1) between the test piece and the face 24. Gap G is preferably, in a typical working embodiment, on the order of less than 0.010 inches, and is typically created by spacing the face plate away from the test piece by means of clamps on a plate which rides the material on rollers. The spacing means, clamps, and the roller-mounted plate are well known in the art and hence require no special illustration herein. Other means for establishing the gap are known and may be used.

The housing defined by body portion 11, gear box 12, and stud plate 14 has a cavity or chamber 26 for a liquid couplant, in particular water. Cavity 26 is formed wholly in body portion 11 and is shaped to include a flared rear portion 28, a transversely cylindrical middle portion 30, and a front portion 32 communicating with a forwardly tapered face plate cavity 34 having an opening 35 providing communication with gap G.

The middle portion 30 of the housing cavity is extended transversely as shown in FIG. 4 to provide, at one side of the cavity, a cylindrical bearing space 36 opening through one side surface of the body portion 11 to receive and rotatably support a cylindrically shaped transducer holder 38 extending across the middle cavity portion 30. The transducer holder 38 is formed, where it extends across the middle portion, with a transducer-receiving bore 40. Referring to FIGS. 1, 2, and 4, a set screw access opening 42 is formed in the underside of the body portion, communicating in one position to which the transducer holder 38 is rotated, with a set screw mounting opening 43 formed in holder 38 and having a reduced, threaded part in which there is engaged a set screw 44 extendable into bore 40 for the purpose of lockably engaging a transducer 46 supported in the bore.

The transducer is conventional per se. The illustrated transducer has a projecting portion 48 for accommodating an electrical cable, not shown, and has a beam-propagating front end surface 50 facing opening 35 within the front cavity portion 32.

Thus, the transducer can be linearly adjusted, that is, adjusted along the path in which it propagates its beam, within bore 40. After being adjusted to establish the desired focal distance between surface 50 and the surface of the test piece exposed within opening 35, the set screw 44 is tightened against the transducer to lock it in the selected position of linear adjustment. This is done with access bore 42 and set screw opening 43 in registry to permit insertion of a screwdriver, after which the transducer holder 38 can be rotatably adjusted about an axis extending transversely of cavity 26 to establish a precise angulated setting of the transducer.

Referring to FIG. 4, a low-friction bearing for holder 38 is provided by mounting, in an end recess 52 of the holder, a ball bearing 54 seated in the headed inner end of a ball bearing stud 56 projecting through a center opening 57 of stud plate 14 and axially bored to accommodate the ball bearing, together with cambered spring washers 58 and set screws 60. These provide for adjustment of the freedom with which the holder 38 may rotate in bore 36, and also permit a takeup for wear of the ball bearing assemblies provided at opposite ends of the transducer holder.

Precise rotatable adjustment of the holder is provided for (see FIGS. 3 and 4) by a gear 62 pinned as at 63 to holder 38 within a clearance recess 64 of gear box 12. A ball bearing 66 provides a low-friction rotatable mounting of gear 62 (and hence of holder 38) and is engaged between the gear 62 and the inner end of a ball bearing support and adjusting screw 68 lockable in selected positions of threaded adjustment by a nut 70.

A worm 72 (FIG. 3) is pinned to and hence rotatable with an elongated shaft 74 the inner end of which rotates in a bushing 76 adjustably positioned in worm gear bore 77 by means of a threaded plunger 78. Intermediate its ends, shaft 74 is rotatable within a bushing 80 secured in place by set screws 82 engaged in a threaded bore 83 of gear box 12.

Shaft 74 projects beyond the rear surface of the housing, where it receives a calibrated dial 84 secured to the shaft for rotation therewith by a set screw 86. The rearwardly projecting extremity of the shaft is provided with a knob 88 lockably engaged with the shaft for the purpose of rotating the same.

Dial 84 has a plurality of indicia 89 (see FIG. 1) which may be numbered, conveniently "1" through "8". Any selected indicium or gradation of the dial may be brought into registration with a marking 91 provided upon the rear surface of the housing (FIG. 2).

Communicating with the forward cavity portion 32 through the bottom of the housing is a water inlet fitting 90, opening into forward cavity portion 32 adjacent a sidewall of the forward cavity portion (see FIG. 4), normally to the path along which the transducer beam is propagated.

The water is thus introduced in a swirling motion, during initial filling of the cavity with the liquid couplant, along a path at the bottom of the cavity and tangential to a wall of the cavity. This has been found effective to prevent entrapment of air within the cavity, and efficiently purges air through an air outlet 92 communicating with the cavity through the top of the housing opposite the water inlet.

In FIGS. 6–10 a second form of the invention is illustrated. The basic operating concept is similar to that of the first form. Thus, there is a housing generally designated 93 having a body portion 94 formed with flat, vertical back and side surfaces, and a flat, inclined, downwardly facing front surface 95 to which a rectangular face plate 96, having a transversely extending, approximately semi-cylindrical test-piece-receiving face 98, is removably attached by a rectangular series of screws 100.

Intermediate its ends (FIG. 8 and 10) face 98 has an opening 102 providing communication between a gap G defined between the test piece and the face 98, and a rearwardly opening face plate cavity 104 communicating with and forming a forward extension of the main cavity or couplant chamber 105 of body portion 94.

Extending into communication with main cavity 105, adjacent the bottom surface of said cavity (see FIG. 6) is a water inlet fitting 106. The water inlet is disposed near the merger of cavity 105 into its forward extension 104. Also in communication with the cavity 105, but opening into the cavity through the top surface thereof a substantial distance rearwardly from the front end of the cavity (see FIG. 10) is an air outlet or exhaust fitting 108 engageable in air exhaust bore 110 of body portion 94.

The front cavity portion 111 upon which the water inlet and air outlet open is closed at its back end by a rectangular transducer holder 112 mounted for vertical sliding movement in a rear portion 113 of cavity 105.

A guide tongue 114 formed upon holder 112 is slidably engaged in vertically extending guide slot 116 formed in one sidewall of the housing 93 (see FIG. 6).

Closing the bottom end of the rear cavity portion 113 is a bottom plate 118 secured to the underside of body portion 94 by screws 120.

The transducer holder 112 is formed (FIG. 10) with an inclined through bore 124 in which a conventional transducer 126 is mounted for linear sliding adjustment, the transducer being manually adjustable along the path in which its beams are propagated from its front surface 127, after which the transducer adjustment is preserved by threading a set screw 128 thereagainst.

Formed in the upper end of the transducer holder 112 is a vertical, threaded bore 130, in which is threadedly engaged a plunger 132, the upper end of which projects beyond the top surface of the housing and is provided with an operating knob 134. A calibrated dial 136, having gradations 137 selectively registrable with an indicium 139 of the housing, is secured to knob 134 for rotation therewith and bears against the top surface of the housing. Within the housing a coil spring 138 is held under compression between the upper end of the transducer holder 112 and a shoulder 140 of the housing.

By rotating knob 134 until the dial has been selectively positioned, the transducer holder is adjustable to a selected location in a vertical direction. This in turn causes the transducer to be bodily adjusted vertically, thus to provide for precise adjustment of the angle of incidence of the beam propagated by the transducer, following axial or linear adjustment thereof for the purpose of selecting the proper focal distance between the transducer and the test piece.

As in the first form of the invention, the modified form shown in FIGS. 6–10 is adapted to permit ready removal and interchange of any of various face plates 96, according to the particular size and diameter of the tubular stock to be tested for flaws. The gap G necessarily existing between the face plate and the test piece is again on the order of less than 0.010 inch. Thereafter, precision adjustment of the transducer holder, and linear adjustment of the transducer within the holder, are effected for the purposes of selecting a precise focal distance and angle of refraction for the propagated beam.

When water is directed into the cavity 105 through inlet 106, it will initially fill the cavity, entering in a swirling motion in a direction generally tangential of the cavity, in the same manner as in the first form of the invention. This assures the purging of air through fitting 108 with minimal possibility of entrapment of the air within the cavity. As soon as the cavity is filled, the outflow of air is shut off, and the flow of water is reduced to just that point where it will make up for losses occurring through opening 102 and its communicating gap G. This flow is maintained throughout the testing of the various test pieces T, after which removal of the test piece will be effective to automatically shut off the inflow of the water couplant.

It is believed that wiring and piping appropriate for controlling the operational cycle within the parameters specified above is sufficiently within the skill of those working in the art as not to require full illustration herein. It is sufficient to note that when the coupler is not against the test material, the water inlet and the air outlet lines, in both forms of the invention, would be closed off by solenoid valves in an associated control station. Thus, flow through water inlet lines 90 or 106, from a source 142 of water under pressure, is at this time prevented by normally closed solenoid valves 144, 146 respectively. The valves are connected in parallel lengths of tubing 148, 150 respectively, each of which provides communication between source 142 and line 90 (FIG. 2) or 106 (FIG. 6). Thereafter, when the coupler is placed upon the test material, valve 144 (the "fill valve") is opened, and water flows therethrough to produce a relatively high filling rate of the cavity. Simultaneously, normally closed solenoid valve 148 (the "air exhaust valve") opens to connect the air outlet line 92 of FIG. 2 or 108 of FIG. 6 to vent 150 which is open to the ambient atmosphere, thus allowing the air in the cavity to escape as the filling water enters.

After a preset time, which may readily be determined by an adjustable time delay relay set to operate when the cavity is filled and all air is purged, the flow of water is switched from fill valve 144 to valve 146 (the "flow control valve") preset to a relatively low flow condition, so as to just compensate for water loss from the gap between the coupler and the surface of the test piece. Valve 144 closes simultaneously with opening of valve 146, and at the same time, the solenoid valve 148 in the air outlet line is closed, thus effectively "sealing" the top of the cavity.

Whenever the coupler is removed from the test material, all the solenoid valves are closed to prevent water loss.

This sequence of actions may be performed manually. Preferably, however, they would be performed automatically in response to signals from a limit switch or other form of position sensor, not shown.

As noted above, it is believed of particular significance that successful operation of the coupler includes the manner in which the fill water is introduced into the cavity, taken with the location of the air outlet connection. The water inlet in both forms of the invention is tangent to one of the sides of the cavity so that the entering water, during the fill cycle, produces the above mentioned swirling action. This helps to propel the air in the cavity toward the air outlet. That outlet in turn is located at the highest point of the cavity portion in which the water couplant is confined, to prevent pockets of air from being trapped in the cavity at the end of the fill cycle.

In a typical, and important application of the invention, it would be utilized in an "on-mill" ultrasonic inspection system for welded tubing as it is being made. In this case, two of the couplers would be located so as to scan the weld line of the tubing from opposite directions. The ability to use immersion type focussed transducers for this test assures a far more uniform coverage of the cross-section of the weld zone than is possible by using contact transducers with curved shoes. This advantage results from the ability to control the incidence angle with extreme precision and uniformity over the entire width of the propagated transducer beam.

The invention has the distinct advantages of conventional immersion transducers, while still being applicable to test material with nearly the convenience of a typical contact transducer (that is, without the requirement for an immersion tank). As herein disclosed, the invention permits the refinements of using focussed immersion transducers with precise adjustment of incidence angle and focal distance. The invention is thus distinguished from prior art "bubblers" or "squirters" in that a small, confined volume of water is utilized between the transducer face and the surface of the test material.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

We claim:

1. In an inspection device, especially for tubular test pieces, an ultrasonic transducer coupler comprising:
   (a) a housing having a cavity for a water couplant, said cavity having an inlet adapted for introducing a liquid couplant, the housing having a bottom and said inlet communicating with the cavity through the bottom of the housing, the inlet opening into the cavity adjacent a side wall of the cavity in a direction to introduce the liquid couplant in a swirling motion at the bottom of the cavity along a path tangential to said wall thereof, the cavity having a high point formed with an air vent, whereby to fill the cavity with said couplant while simultaneously exhausting air through the outlet;
   (b) a transducer holder mounted in the housing within the cavity;
   (c) a transucer carried by the holder and having a lens through which an ultrasonic beam is directed through the cavity from the transducer;
   (d) means carried by the housing for effecting precision adjustments of the transducer holder;
   (e) a face plate having a face contoured to complement the contour of the test piece being inspected with a narrow gap being left therebetween, said face plate having an opening in communication with the cavity, the opening being coincident with the path along which the beam from the transducer is propagated for passage of the beam through the opening against a test piece that is being inspected, the inlet for the liquid couplant opening into the cavity substantially normally to the path along which the transducer beam is propagated whereby the couplant will be introduced in a path swirling about the path of the beam; and
   (f) means for shutting off the air outlet to the further exhaustion of air therethrough when the cavity is completely filled, whereby upon filling of the cavity with the couplant the outflow of air will be terminated, with further flow of the couplant into the cavity being at a rate sufficient to replace, on a continuing basis, couplant exiting the cavity via the face plate opening and said gap.

2. In an inspection device, especially for tubular test pieces, an ultrasonic transducer coupler as in claim 1 including means, independent of the holder adjustment means, for adjusting the transducer in repect to the holder, the transducer being adjustable in respect to its holder in a linear direction toward and away from the face plate opening, each adjustment of the transucer in respect to the holder in said linear direction being confined to said path substantially normal to that along which the liquid couplant is introduced to the cavity.

3. In an inspection device, especially for tubular test pieces, an ultrasonic transducer coupler as in claim 2 in which the linear adjustment of the transducer is along the path of the focussed beam thereof, for selective adjustment of the focal distance between the transducer and the test piece.

4. In an inspection device, especially for tubular test pieces, an ultrasonic transducer coupler as in claim 1 in which the holder adjustment is about an axis extending transversely of the housing cavity, the trandsucer being adjustable within the holder in each position to which the holder is adjusted about said axis, along a linear path intersecting said axis, the transducer holder being in the form of a rotatably adjustable cylinder extending across the housing cavity and having a transverse bore in which the transducer is mounted for slidable adjustment toward and away from the opening of the face plate.

5. In an inspection device, especially for tubular test pieces, an ultrasonic transducer coupler as in claim 4 including means carried by the holder for locking the transducer in selected positions to which it is adjusted within the holder.

6. In an inspection device, especially for tubular test pieces, an ultransonic transducer coupler as in claim 4 in which the holder means for adjusting the transducer holder includes a worm mounted in the housing, a calibrated dial and knob mounted on the worm for ready accessibility to a user, and a gear in mesh with the worm and secured to the cylinder for rotation therewith about said axis.

7. The method of ultrasonically inspecting a test piece that comprises the steps of:
 (a) coupling a transducer to a test piece while providing a cavity therebetween and a gap between the cavity and the test piece;
 (b) connecting the cavity to a pressurized source for a liquid couplant and to an air exhaust vent;
 (c) forcing the couplant into the cavity at the bottom of the cavity in a swirling path of flow and maintaining said swirling flow path until the cavity is filled with the couplant;
 (d) simultaneously with filling the cavity, exhausting air therefrom through said vent;
 (e) when the cavity is filled, sealing off the air vent while simultaneously adjusting the inflow of liquid couplant into the cavity along its swirling path to a rate just sufficient to replace any couplant leaked from the cavity through the gap, to maintain the cavity in a filled condition while said transducer is coupled to the test piece;
 (f) terminating the inflow of water at times when the transducer and test piece are not coupled; and
 (g) when the transducer and test piece are coupled, directing said beams against the test piece through the swirling flow path of said couplant.

* * * * *